United States Patent
Shirai et al.

(10) Patent No.: US 10,863,958 B2
(45) Date of Patent: Dec. 15, 2020

(54) X-RAY PHASE DIFFERENCE IMAGING SYSTEM AND PHASE CONTRAST IMAGE CORRECTION METHOD

(71) Applicant: Shimadzu Corporation, Kyoto (JP)

(72) Inventors: Taro Shirai, Kyoto (JP); Kenji Kimura, Kyoto (JP); Takahiro Doki, Kyoto (JP); Satoshi Sano, Kyoto (JP); Akira Horiba, Kyoto (JP); Naoki Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/636,737

(22) PCT Filed: Sep. 18, 2018

(86) PCT No.: PCT/JP2018/034493
§ 371 (c)(1),
(2) Date: Feb. 5, 2020

(87) PCT Pub. No.: WO2019/073760
PCT Pub. Date: Apr. 18, 2019

(65) Prior Publication Data
US 2020/0196969 A1    Jun. 25, 2020

(30) Foreign Application Priority Data

Oct. 11, 2017  (JP) .................. 2017-197928

(51) Int. Cl.
*A61B 6/00*    (2006.01)

(52) U.S. Cl.
CPC ............ *A61B 6/484* (2013.01); *A61B 6/4291* (2013.01); *A61B 6/583* (2013.01)

(58) Field of Classification Search
CPC ........ A61B 6/484; A61B 6/4291; A61B 6/583
USPC .......................................................... 378/62
See application file for complete search history.

(56) References Cited

U.S. PATENT DOCUMENTS

| | | | |
|---|---|---|---|
| 2010/0290590 A1* | 11/2010 | Ouchi | G01N 23/20075 378/62 |
| 2011/0261924 A1* | 10/2011 | Bredno | A61B 6/032 378/9 |
| 2012/0106705 A1* | 5/2012 | Mikami | A61B 6/4291 378/70 |
| 2012/0114098 A1* | 5/2012 | Mikami | A61B 6/4233 378/62 |

(Continued)

FOREIGN PATENT DOCUMENTS

JP    2015-71051 A    4/2015

OTHER PUBLICATIONS

International Search Report dated Nov. 27, 2018 in corresponding International Application No. PCT/JP2018/034493; 3 pages.

(Continued)

*Primary Examiner* — Taeho Jo
(74) *Attorney, Agent, or Firm* — Maier & Maier, PLLC

(57) ABSTRACT

This X-ray phase difference imaging system (100) includes an X-ray source (1), a plurality of gratings, a detector (4), and an image processor (6), in which the image processor (6) is configured to correct an artifact of a second phase contrast image (10b) that is reconstructed by using a first X-ray image (9a) and a third X-ray image (9c), on the basis of a first phase contrast image (10a) that is reconstructed by using the first X-ray image (9a) and a second X-ray image (9b).

13 Claims, 11 Drawing Sheets

(56) References Cited

U.S. PATENT DOCUMENTS

| | | | | |
|---|---|---|---|---|
| 2012/0140885 | A1* | 6/2012 | Iwakiri | A61B 6/4291 378/62 |
| 2012/0145912 | A1* | 6/2012 | Iwakiri | A61B 6/06 250/370.08 |
| 2012/0153177 | A1* | 6/2012 | Iwakiri | A61B 6/4021 250/370.09 |
| 2012/0163554 | A1* | 6/2012 | Tada | A61B 6/4291 378/154 |
| 2013/0011040 | A1* | 1/2013 | Kido | A61B 6/548 382/132 |
| 2014/0126690 | A1* | 5/2014 | Yamaguchi | A61B 6/484 378/36 |
| 2014/0185757 | A1* | 7/2014 | Sperl | G06T 11/003 378/62 |
| 2015/0071403 | A1* | 3/2015 | Ishii | A61B 6/5282 378/36 |
| 2016/0109387 | A1* | 4/2016 | Pan | G01N 23/041 378/36 |
| 2018/0042571 | A1* | 2/2018 | Sano | G01N 23/043 |
| 2018/0172607 | A1* | 6/2018 | Sano | A61B 6/4035 |
| 2018/0182131 | A1* | 6/2018 | Koehler | A61B 6/4208 |

OTHER PUBLICATIONS

Written Opinion dated Nov. 27, 2018 in corresponding International Application No. PCT/JP2018/034493; 4 pages; Machine translation attached.

F. Pfeiffer et al., "Hard-X-ray dark-field imaging using a grating interferometer", Nature Materials, Jan. 13, 2008; pp. 1-4.

Atsushi Momose et al., "Grating-Based X-ray Phase Imaging Using Multiline X-ray Source", Japanese Journal of Applied Physics 48, Jul. 21, 2009; pp. 76512-1 to 76512-5.

\* cited by examiner

FIG. 4
FIRST EMBODIMENT
(A) FIRST X-RAY IMAGE
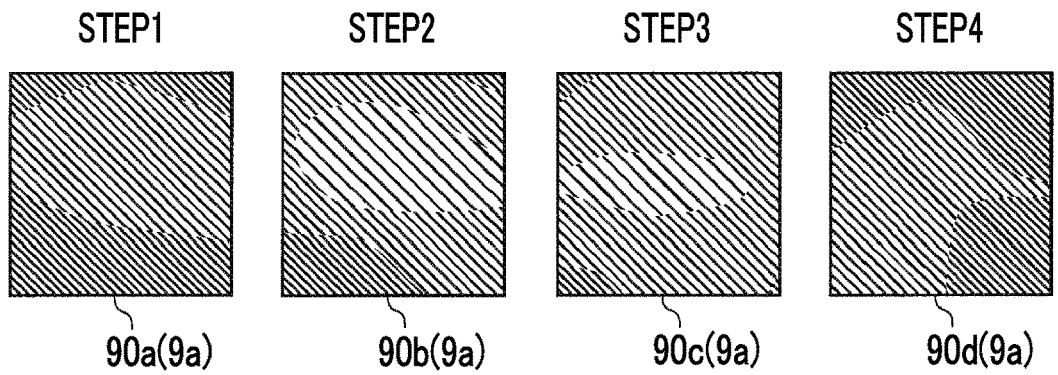
(B) SECOND X-RAY IMAGE
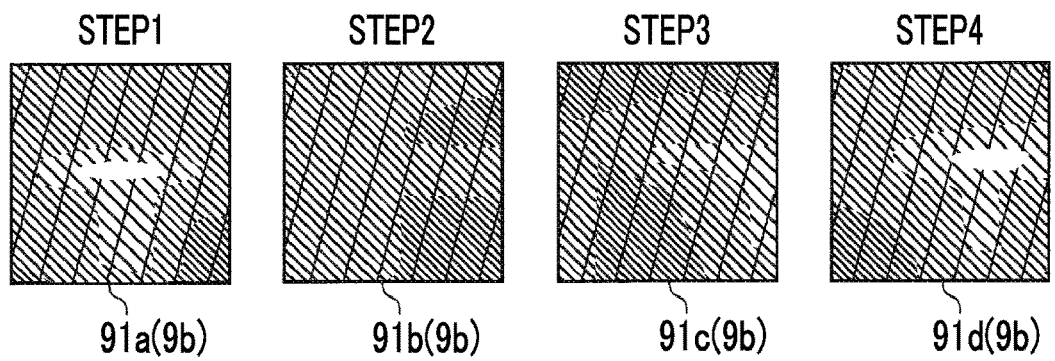
(C) FIRST PHASE CONTRAST IMAGE
(DARK FIELD IMAGE)
BEFORE FILTERING PROCESS
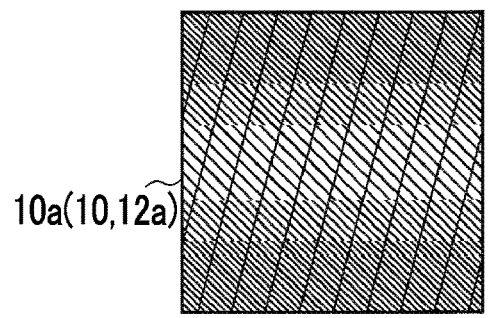
(D) FIRST PHASE CONTRAST IMAGE
(DARK FIELD IMAGE)
AFTER FILTERING PROCESS
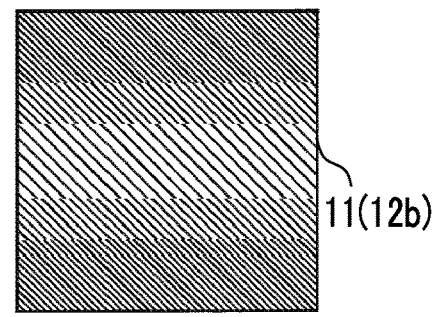

FIG. 5
FIRST EMBODIMENT
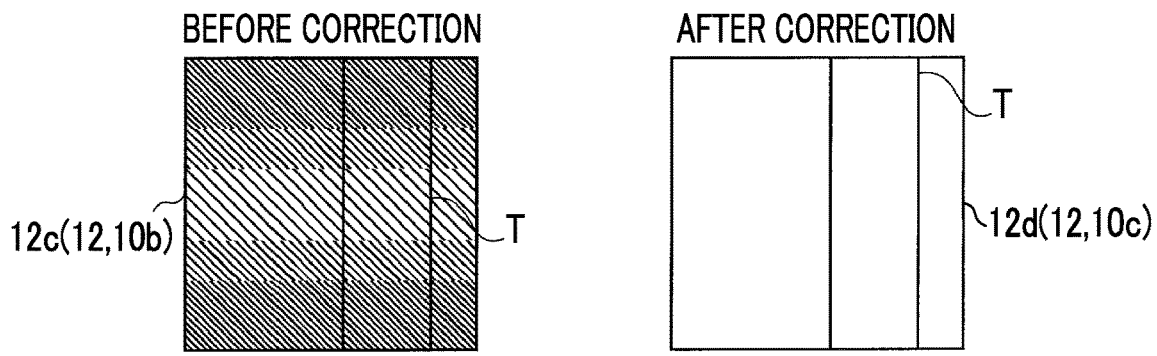
(A) DARK FIELD IMAGE
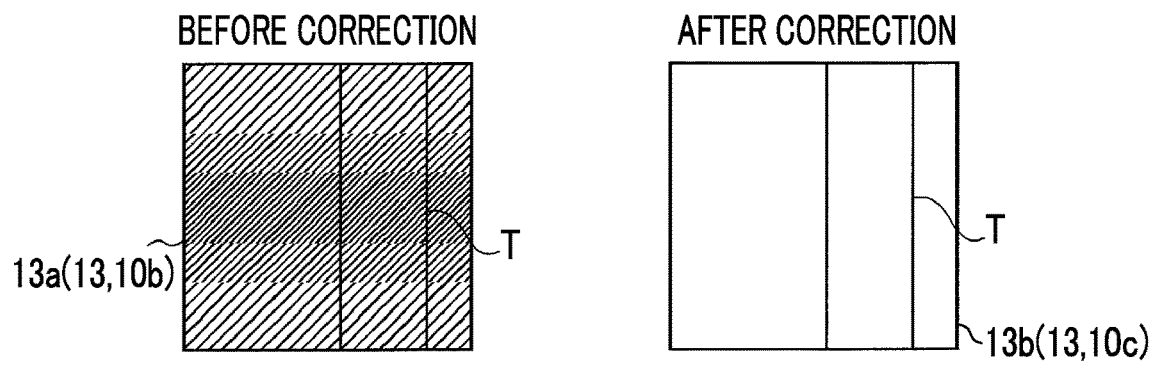
(B) ABSORPTION IMAGE
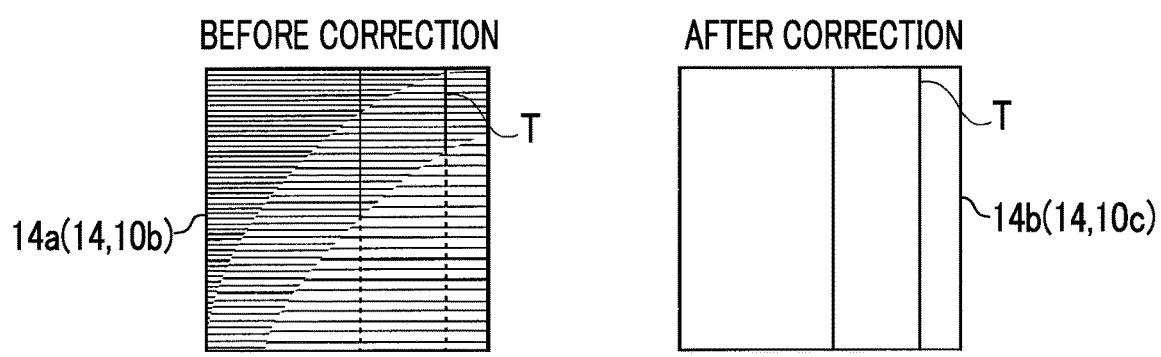
(C) PHASE DIFFERENTIATION IMAGE FIG. 10
THIRD MODIFICATION EXAMPLE OF FIRST EMBODIMENT
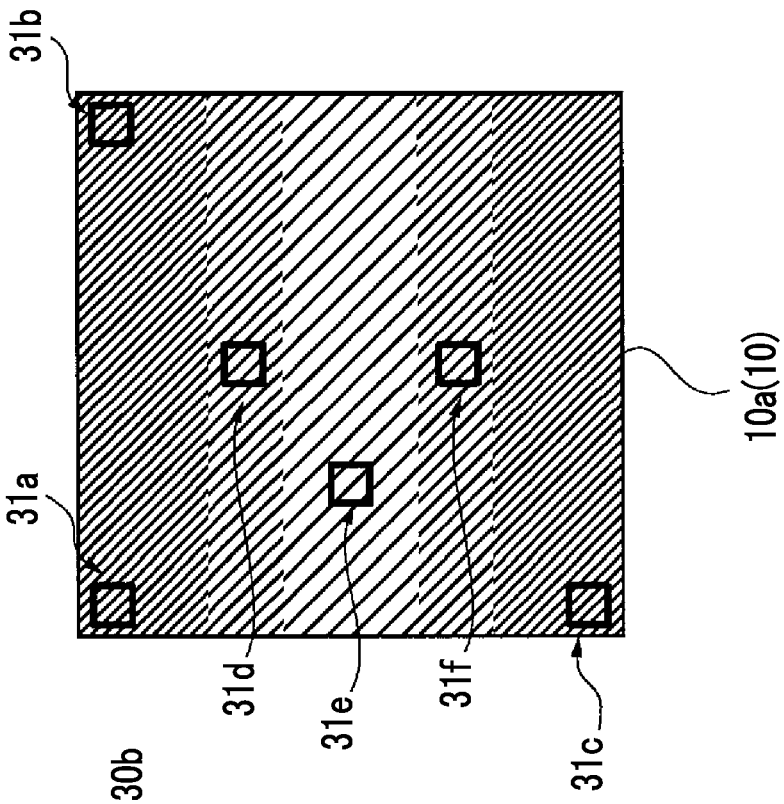
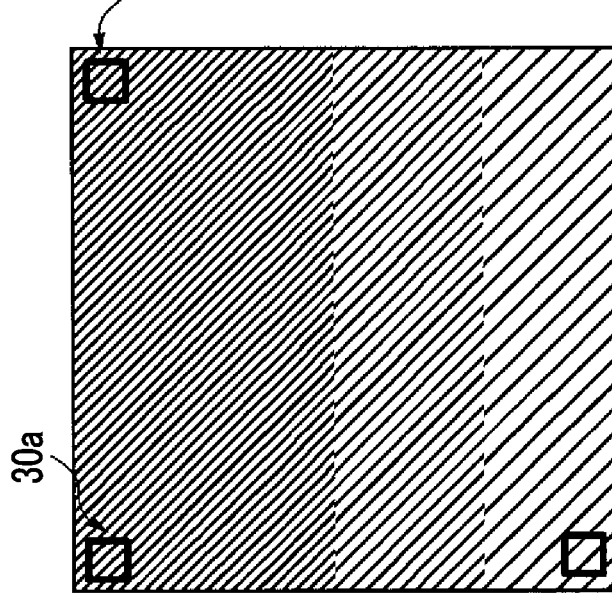

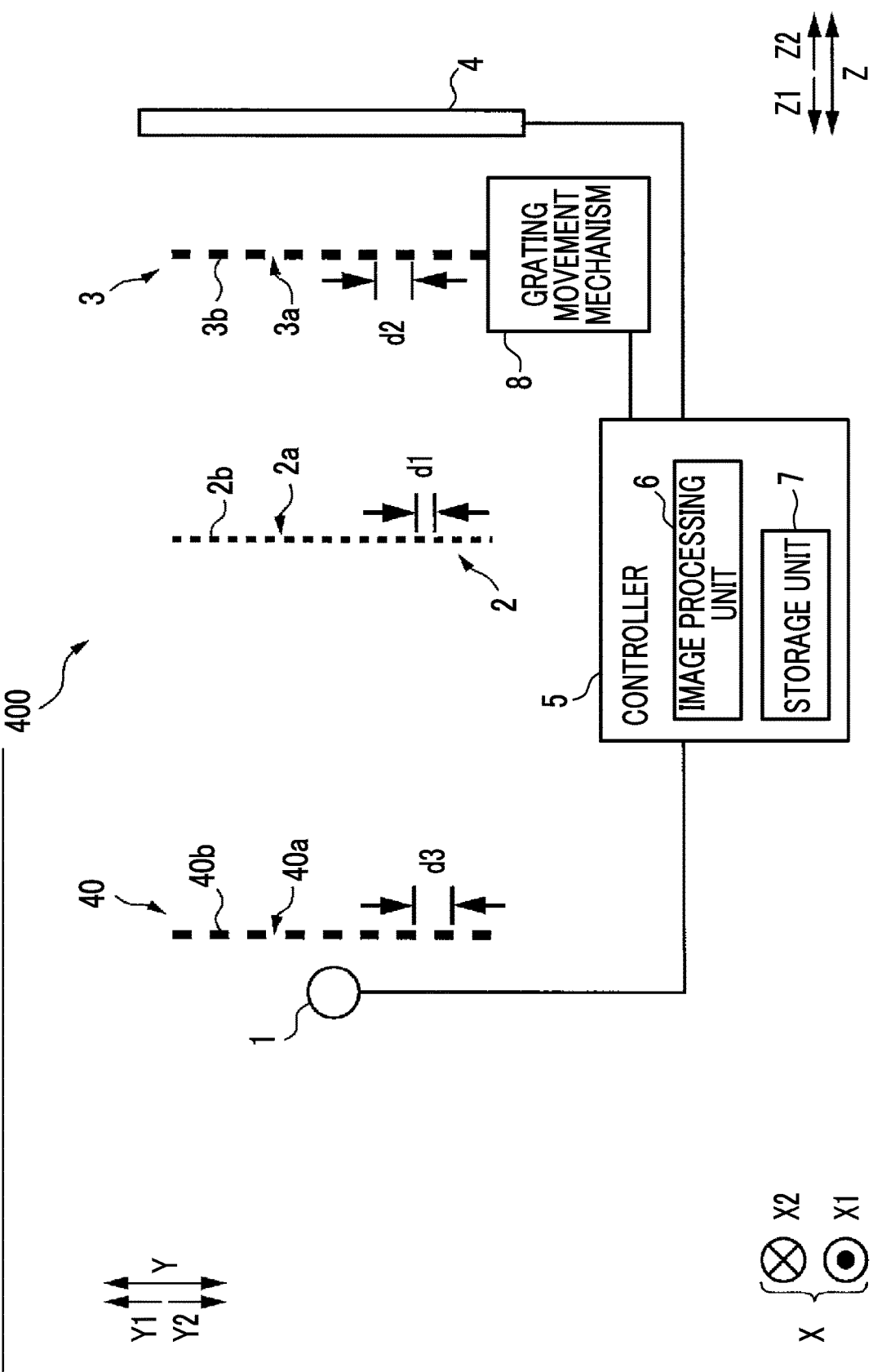

X-RAY PHASE DIFFERENCE IMAGING SYSTEM AND PHASE CONTRAST IMAGE CORRECTION METHOD

FIELD

The present invention relates to an X-ray phase difference imaging system and a phase contrast image correction method, and particularly to an X-ray phase difference imaging system performing imaging by using a plurality of gratings and a phase contrast image correction method.

BACKGROUND

In the related art, there are an X-ray phase difference imaging system performing imaging by using a plurality of gratings and a phase contrast image correction method. Such an X-ray phase difference imaging system is disclosed in Japanese Unexamined Patent Application Publication No. 2015-71051 (PTL 1).

The X-ray phase difference imaging system disclosed in PTL 1 is configured to perform X-ray image with a Talbot-Lau interferometer so as to generate a phase contrast image.

Here, the Talbot-Lau interferometer performs imaging by using a total of three gratings such as a multi-slit, a phase grating, and an absorption grating, disposed between an X-ray source and a detector. Specifically, a phase contrast image is generated according to a fringe scanning method in which imaging is performed by translating any one of the three gratings in a direction orthogonal to a pattern of the grating, or a moire single shot method in which the phase grating or the absorption grating is rotated by a minute angle about an optical axis of an X-ray such that a moire fringe is caused, and thus imaging is performed. In either method, in the Talbot-Lau interferometer, an X-ray phase contrast image is generated by using an image captured in a state in which a subject is not disposed and an image captured in a state in which the subject is disposed. Therefore, in a case where an imaging condition changes between imaging performed in a state in which a subject is not disposed and imaging performed in a state in which the subject is disposed, an artifact occurs. The change in the imaging condition indicates that, for example, relative positions of a plurality of gratings change during imaging of respective X-ray images. Specifically, the change in the imaging condition occurs due to deviation in relative positions of the plurality of gratings when a grating holding portion holding each grating is thermally expanded due to heat generated from an X-ray source or is vibrated. Therefore, positional deviation of the relative positions of the plurality of gratings due to thermal expansion or vibration of the grating holding portions increases with the passage of time. In other words, the imaging condition changes with the passage of time. The influence of an artifact occurring in an acquired phase contrast image increases according to the extent of the change in the imaging condition.

The X-ray phase difference imaging system disclosed in PTL 1 is configured to correct the artifact of the phase contrast image by approximating the artifact by using an acquired X-ray image. Specifically, the X-ray phase difference imaging system disclosed in PTL 1 approximates the artifact on the basis of pixel values of a plurality of regions of a background portion in which the subject is not captured in the X-ray image, and thus corrects the artifact occurring in the phase contrast image.

[PTL 1] Japanese Unexamined Patent Application Publication No. 2015-71051

SUMMARY

However, in the configuration disclosed in PTL 1, since an artifact is approximated on the basis of pixel values of a plurality of regions of a background portion in which the subject is not captured in the X-ray image, there is a problem in that, in a case where a subject is captured in the whole or most of a captured image, for example, the subject is enlarged to be captured, an artifact due to positional deviation of a plurality of gratings cannot be corrected.

The present invention has been made to solve the problem, and one object of the present invention is to provide an X-ray phase difference imaging system and a phase contrast image correction method capable of correcting an artifact caused by a change in an imaging condition even in a case where an image is captured such that a subject is captured in the whole or most of the captured image.

In order to achieve the object, according to a first aspect of the present invention, there is provided an X-ray phase difference imaging system including an X-ray source; a plurality of gratings that include a first grating irradiated with an X-ray from the X-ray source, and a second grating irradiated with the X-ray from the first grating; a detector that detects the X-ray irradiated from the X-ray source; and an image processor that generates a phase contrast image by using an X-ray image detected by the detector, in which the image processor is configured to acquire a first X-ray image captured in a state in which a subject is not disposed, acquire a second X-ray image captured in a state in which the subject is not disposed and a third X-ray image captured in a state in which the subject is disposed after the first X-ray image is acquired, reconstruct a first phase contrast image by using the first X-ray image and the second X-ray image that are captured such that a time interval between capturing of the second X-ray image and capturing of the third X-ray image is shorter than a time interval between capturing of the first X-ray image and capturing of the third X-ray image, reconstruct a second phase contrast image by using the first X-ray image and the third X-ray image, and correct an artifact of the second phase contrast image on the basis of the first phase contrast image.

Here, in a case where an imaging interval is long, there is a probability that a positional deviation may occur in a relative position between gratings of a plurality of gratings due to thermal expansion or vibration of grating holding portions holding the gratings. As an imaging interval becomes longer, a probability that a positional deviation may occur in a relative position between gratings of a plurality of gratings increases, and thus the influence of an artifact occurring in an acquired phase contrast image becomes greater. Therefore, as described above, the X-ray phase difference imaging system in the first aspect of the present invention is configured to reconstruct the first phase contrast image by using the first X-ray image and the second X-ray image that are captured such that the time interval between capturing of the second X-ray image and capturing of the third X-ray image is shorter than the time interval between capturing of the first X-ray image and the third X-ray image, and correct an artifact of the second phase contrast image on the basis of the first phase contrast image. Consequently, it is possible to suppress a change in an imaging condition in capturing of the second X-ray image and capturing of the third X-ray image. As a result, it is possible to handle an artifact occurring in the first phase contrast image and an artifact occurring in the second phase contrast image as the substantially same artifact. Therefore, it is possible to correct an artifact caused by a change in an imaging condition on the basis of the first phase contrast image reconstructed by using the first X-ray image and the second X-ray image. Since the first X-ray image and the second X-ray image are images captured in a state in which the subject is not disposed, even in a case where the subject is imaged to be captured in the whole or most of a captured image, it is possible to correct an artifact caused by a change in an imaging condition in the second phase contrast image.

In the X-ray phase difference imaging system according to the first aspect, preferably, the image processor is configured to reconstruct the first phase contrast image by using the second X-ray image that is captured in a manner that one of capturing of the second X-ray image and capturing of the third X-ray image is performed and subsequently the other is performed, and the first X-ray image. With this configuration, the second X-ray image and the third X-ray image can be successively captured, and thus it is possible to reduce the time interval between capturing of the second X-ray image and capturing of the third X-ray image. As a result, even in a case where an imaging condition changes between capturing of the second X-ray image and capturing of the third X-ray image, it is possible to reduce the influence of an artifact caused by the change in the imaging condition and thus to further improve the correction effect for the second phase contrast image.

In this case, preferably, the image processor is configured to reconstruct the first phase contrast image by using the second X-ray image captured right before or right after the third X-ray image is captured, and the first X-ray image. With this configuration, it is possible to further reduce the time interval between capturing of the second X-ray image and capturing of the third X-ray image. As a result, even in a case where an imaging condition changes between capturing of the second X-ray image and capturing of the third X-ray image, it is possible to further suppress the influence of an artifact caused by the change in the imaging condition and thus to still further improve the correction effect for the second phase contrast image. The phrase "right before and right after capturing of the third X-ray image" indicates that imaging is performed within a predetermined time interval before and after the third X-ray image is captured. The predetermined time interval is a time interval that is within a predetermined time for which an imaging condition may be regarded as substantially not changing with the passage of time (a substantially identical imaging condition may be regarded as being maintained), and is, for example, 30 minutes.

In the X-ray phase difference imaging system according to the first aspect, preferably, the image processor is configured to correct an artifact of the second phase contrast image on the basis of the first phase contrast image reconstructed by using the first X-ray image and the second X-ray image that are captured such that a first exposure time of the X-ray when the second X-ray image is captured is shorter than a second exposure time of the X-ray when the first X-ray image is captured. With this configuration, the first exposure time is shorter than the second exposure time, and thus it is possible to reduce an imaging time more than in a case where the third X-ray image is captured after the first X-ray image is captured.

In this case, preferably, the first exposure time is a predetermined time for which the second X-ray image having image quality allowing a tendency of an artifact to be identified can be captured. Here, the first X-ray image preferably has high image quality in order to improve the image quality of the second phase contrast image. On the other hand, the second X-ray image may have the lowest image quality since a tendency of an artifact has only to be identifiable in the first phase contrast image. Therefore, the first exposure time can be made shorter in a range in which a tendency of an artifact is identifiable, and thus an imaging time can be further reduced.

Preferably, the X-ray phase difference imaging system according to the first aspect further includes a storage that stores the first X-ray image, and the image processor is configured to reconstruct the first phase contrast image and the second phase contrast image by using the first X-ray image stored in the storage. With this configuration, the first X-ray image captured in advance is stored in the storage, and thus it is possible to generate the first phase contrast image and the second phase contrast image without acquiring the first X-ray image at every imaging.

In the X-ray phase difference imaging system according to the first aspect, preferably, an artifact of the phase contrast image is a gradational artifact occurring in the first phase contrast image and the second phase contrast image. Consequently, since an artifact caused by a change in an imaging condition with the passage of time is gradational, the present invention is irradiated, and thus it is possible to effectively correct the gradational artifact occurring in the second phase contrast image.

In the X-ray phase difference imaging system according to the first aspect, preferably, the image processor is configured to acquire correction data in which an artifact of the first phase contrast image is reflected, by using a polynomial expression including at least a linear function or a quadratic function. With this configuration, it is possible to acquire the correction data in which an artifact is easily reflected by using the polynomial expression.

In this case, preferably, the image processor is configured to acquire the correction data in which the artifact of the first phase contrast image is reflected, on the basis of pixel values of a plurality of regions in the first phase contrast image. With this configuration, it is possible to acquire the more accurate correction data in which the artifact is reflected.

In the X-ray phase difference imaging system according to the first aspect, preferably, the image processor is configured to acquire correction data in which an artifact of the first phase contrast image is reflected, through a filtering process using at least a smoothing filter or a low-pass filter. With this configuration, noise of the first phase contrast image can be removed through the filtering process, and thus it is possible to correct an artifact without increasing noise of the second phase contrast image.

In the X-ray phase difference imaging system according to the first aspect, preferably, the plurality of gratings further include a third grating that is disposed between the X-ray source and the first grating. With this configuration, it is possible to increase coherence of an X-ray irradiated from the X-ray source by using the third grating. As a result, a self-image of the first grating can be formed without depending on a focal diameter of the X-ray source, and thus it is possible to improve the degree of freedom of selection of the X-ray source.

According to a second aspect of the present invention, there is provided an X-ray phase difference imaging system including an X-ray source; a plurality of gratings that include a first grating irradiated with an X-ray from the X-ray source, and a second grating irradiated with the X-ray from the first grating; a detector that detects the X-ray irradiated from the X-ray source; and an image processor that generates a phase contrast image by using an X-ray image detected by the detector, in which the image processor is configured to acquire a first X-ray image captured in a state in which a subject is not disposed, acquire a second X-ray image captured in a state in which the subject is not disposed and a third X-ray image captured in a state in which the subject is disposed after the first X-ray image is acquired, reconstruct a first phase contrast image by using the first X-ray image and the second X-ray image, reconstruct a second phase contrast image by using the first X-ray image and the third X-ray image, and correct an artifact of the second phase contrast image on the basis of the first phase contrast image.

In the X-ray phase difference imaging system according to the second aspect of the present invention, with this configuration, it is possible to correct an artifact caused by a change in an imaging condition on the basis of the first phase contrast image reconstructed by using the first X-ray image and the second X-ray image. Since the first X-ray image and the second X-ray image are images captured in a state in which the subject T is not disposed, even in a case where the subject is imaged to be captured in the whole or most of a captured image, it is possible to correct an artifact caused by a change in an imaging condition in the second phase contrast image.

According to a third aspect of the present invention, there is provided a phase contrast image correction method including a step of capturing a first X-ray image in a state in which a subject is not disposed; a step of capturing a second X-ray image in a state in which the subject is not disposed; a step of capturing a third X-ray image in a state in which the subject is disposed before or after the second X-ray image is captured; a step of reconstructing a first phase contrast image by using the first X-ray image and the second X-ray image that are captured such that a time interval between capturing of the second X-ray image and capturing of the third X-ray image is shorter than a time interval between capturing of the first X-ray image and capturing of the third X-ray image; a step of reconstructing a second phase contrast image by using the first X-ray image and the third X-ray image; and a step of correcting an artifact of the second phase contrast image on the basis of the first phase contrast image.

The phase contrast image correction method according to the third aspect of the present invention includes the step of correcting an artifact of the second phase contrast image on the basis of the first phase contrast image that is reconstructed by using the first X-ray image and the second X-ray image that are captured such that the time interval between capturing of the second X-ray image and capturing of the third X-ray image is shorter than the time interval between capturing of the first X-ray image and the third X-ray image. Consequently, the second X-ray image and the third X-ray image can be captured in a state in which an imaging condition does not change. As a result, it is possible to provide the phase contrast image correction method capable of correcting an artifact caused by a change in an imaging condition on the basis of the first phase contrast image reconstructed by using the first X-ray image and the second X-ray image. Since the first X-ray image and the second X-ray image are images captured in a state in which the subject T is not disposed, even in a case where the subject is imaged to be captured in the whole or most of a captured image, it is possible to provide the phase contrast image correction method capable of correcting an artifact caused by a change in an imaging condition in the second phase contrast image.

Advantageous Effects of Invention

According to the present invention, it is possible to provide an X-ray phase difference imaging system and a phase contrast image correction method capable of correcting an artifact caused by a change in an imaging condition even in a case where an image is captured such that a subject is captured in the whole or most of the captured image.

BRIEF DESCRIPTION OF DRAWINGS

FIG. 4(A) is a schematic diagram illustrating a first X-ray image.

FIG. 4(B) is a schematic diagram illustrating a second X-ray image.

FIG. 4(C) is a schematic diagram illustrating a first phase contrast image.

FIG. 4(D) is a schematic diagram illustrating correction data in which an artifact is reflected.

FIG. 5(A) is a schematic diagram illustrating a dark field image generated by the X-ray phase difference imaging system according to the first embodiment of the present invention.

FIG. 5(B) is a schematic diagram illustrating an absorption image.

FIG. 5(C) is a schematic diagram illustrating a phase differentiation image.

FIG. 10(A) is a schematic diagram for describing a process of acquiring correction data in which an artifact is reflected, acquired by an X-ray phase difference imaging system according to a third modification example of the first embodiment of the present invention.

FIG. 10(B) is another schematic diagram for describing a process of acquiring correction data in which an artifact is reflected, acquired by an X-ray phase difference imaging system according to a third modification example of the first embodiment of the present invention.

FIG. 11 is a schematic diagram in which an X-ray phase difference imaging system according to a fourth modification example of the first embodiment of the present invention is viewed from the X direction.

DETAILED DESCRIPTION

Hereinafter, embodiments of the present invention will be described with reference to the drawings.

First Embodiment

With reference to FIGS. 1 to 6, a description will be made a configuration of an X-ray phase difference imaging system 100 according to the first embodiment of the present invention, and a method in which the X-ray phase difference imaging system 100 generates a phase contrast image 10.

(Configuration of X-ray Phase Difference Imaging System)

First, with reference to FIG. 1, a description will be made of a configuration of the X-ray phase difference imaging system 100 according to the first embodiment of the present invention.

Figure 1:
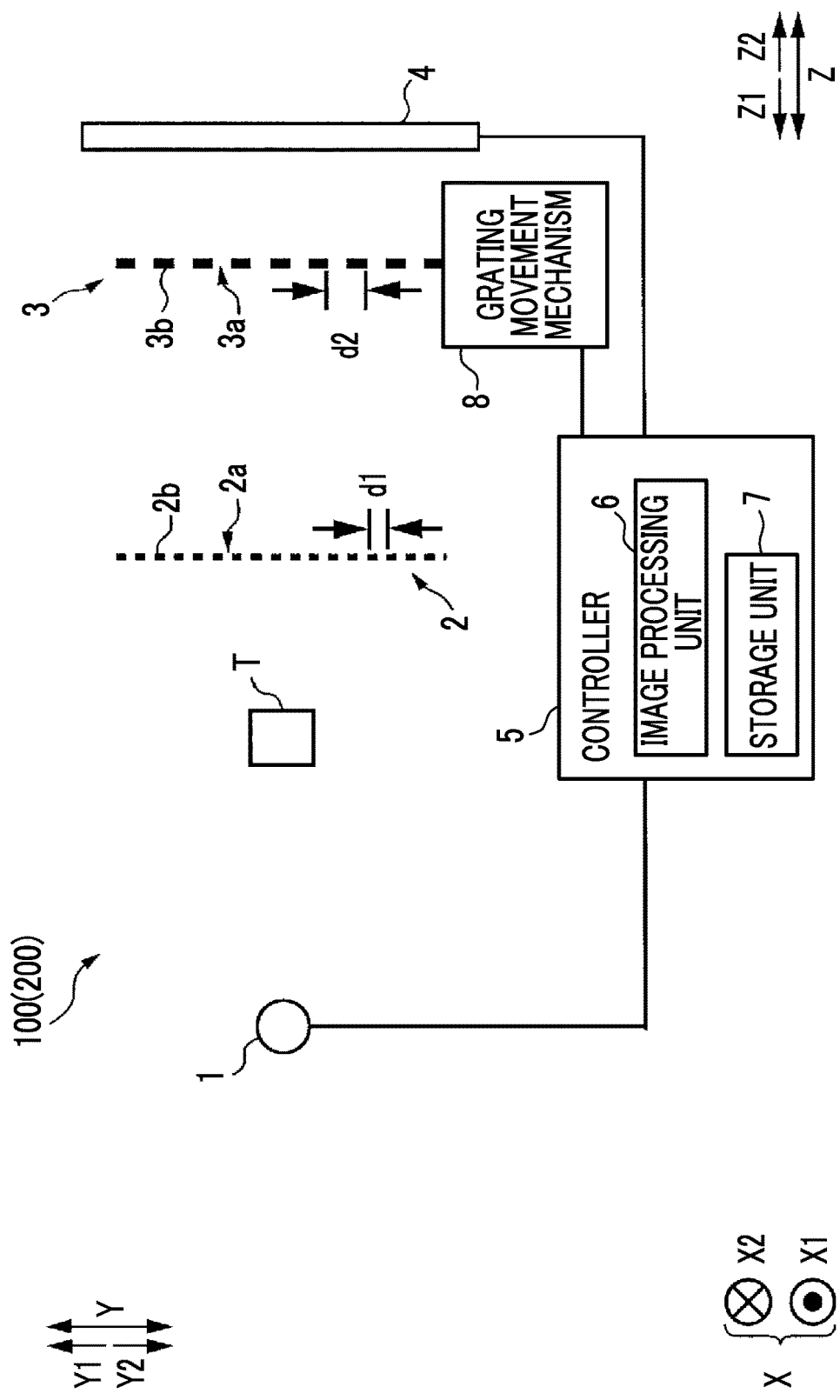
FIG. 1 is a schematic diagram in which an X-ray phase difference imaging system according to a first embodiment of the present invention is viewed from an X direction.

FIG. 1 is a diagram in which the X-ray phase difference imaging system 100 is viewed from an X direction. As illustrated in FIG. 1, the X-ray phase difference imaging system 100 includes an X-ray source 1, a first grating 2, a second grating 3, a detector 4, and a controller 5. In the present specification, a direction from the X-ray source 1 toward the first grating 2 is referred to as a Z2 direction, and a reverse direction thereto is referred to as a Z1 direction. A leftward-rightward direction in a plane orthogonal to the Z direction is referred to as an X direction, a direction rearward of the drawing surface is referred to as an X2 direction, and a direction frontward of the drawing surface is referred to as an X1 direction. An upward-downward direction in a plane orthogonal to the Z direction is referred to as a Y direction, and an upward direction is referred to as a Y1 direction, and a downward direction is referred to as a Y2 direction.

The X-ray source 1 is configured to generate an X-ray due to being supplied with a high voltage on the basis of a signal from the controller 5, and to apply the generated X-ray in the Z2 direction.

The first grating 2 has a plurality of slits 2$a$ and X-ray phase changing portions 2$b$ that are arranged in a predetermined cycle (pitch) d1 in the Y direction. Each of the slits 2$a$ and the X-ray phase changing portions 2$b$ is formed to linearly extend. Each of the slits 2$a$ and the X-ray phase changing portions 2$b$ is formed to extend in parallel. The first grating 2 is a so-called phase grating.

The first grating 2 is disposed between the X-ray source 1 and the second grating 3, and is irradiated with an X-ray from the X-ray source 1. The first grating 2 is provided to form a self-image (not illustrated) of the first grating 2 by using a Talbot effect. In a case where a coherent X-ray passes through a grating with slits, an image (self-image) of the grating is formed at a position separated from the grating by a predetermined distance (Talbot distance). This is referred to as the Talbot effect.

The second grating 3 has a plurality of X-ray transmission portions 3$a$ and X-ray absorption portions 3$b$ arranged in a predetermined cycle (pitch) d2 in the Y direction. Each of the X-ray transmission portions 3$a$ and the X-ray absorption portions 3$b$ is formed to linearly extend. Each of the X-ray transmission portions 3$a$ and the X-ray absorption portions 3$b$ is formed to extend in parallel. The second grating 3 is a so-called absorption grating. The first grating 2 and the second grating 3 are gratings having different functions, but the slit 2$a$ and the X-ray transmission portion 3$a$ transmit an X-ray therethrough. The X-ray absorption portion 3$b$ has a function of blocking an X-ray, and the X-ray phase changing portion 2$b$ changes a phase of the X-ray on the basis of a refractive index difference from the slit 2$a$.

The second grating 3 is disposed between the first grating 2 and the detector 4, and is irradiated with an X-ray having passed through the first grating 2. The second grating 3 is disposed at a position separated from the first grating 2 by the Talbot distance. The second grating 3 interferes with a self-image of the first grating 2, and thus forms a moire fringe (not illustrated) on a detection surface of the detector 4.

The detector 4 is configured to detect an X-ray, convert the detected X-ray into an electric signal, and read the electric signal obtained through conversion as an image signal. The detector 4 is, for example, a flat panel detector (FPD). The detector 4 includes a plurality of conversion elements (not illustrated) and pixel electrodes (not illustrated) disposed on the plurality of conversion elements. The plurality of conversion elements and pixel electrodes are arranged in an array form in a predetermined cycle (pixel pitch) in the X direction and the Y direction. The detector 4 is configured to output the acquired image signal to the controller 5.

The controller 5 is configured to apply an X-ray via the X-ray source 1. The controller 5 includes an image processor 6, and is configured to generate an X-ray image 9 (refer to FIG. 2) and the phase contrast image 10 (refer to FIG. 2) on the basis of the image signal output from the detector 4. The controller 5 includes a storage 7 storing the captured X-ray image 9. The controller 5 is configured to move the second grating 3 stepwise in a grating plane in a direction (Y direction) orthogonal to a grating direction (X direction) via a grating movement mechanism 8. The controller 5 includes a processor such as a central processing unit (CPU).

The image processor 6 is configured to generate a first X-ray image 9$a$ (refer to FIG. 2), a second X-ray image 9$b$ (refer to FIG. 2), and a third X-ray image 9$c$ (refer to FIG. 2) on the basis of image signals output from the detector 4. The image processor 6 is configured to reconstruct a first phase contrast image 10$a$ (refer to FIG. 2) by using the first X-ray image 9$a$ and the second X-ray image 9$b$. The image processor 6 is configured to reconstruct a second phase contrast image 10$b$ (refer to FIG. 2) by using the first X-ray image 9$a$ and the third X-ray image 9$c$. A detailed configuration of reconstructing the first phase contrast image 10$a$ and the second phase contrast image 10$b$ will be described later. The image processor 6 includes a processor such as a graphics processing unit (GPU), or a field-programmable gate array (FPGA) for image processing.

The storage 7 is configured to store the X-ray image generated by the image processor 6. The storage 7 includes, for example, a hard disk drive (HDD).

The grating movement mechanism 8 is configured to move the second grating 3 stepwise in the grating plane (in an XY plane) in the direction (Y direction) orthogonal to the grating direction on the basis of a signal from the controller 5. Specifically, the grating movement mechanism 8 divides the cycle d2 of the second grating 3 by n, and moves the second grating 3 stepwise by d2/n. The grating movement mechanism 8 is configured to move the first grating 2 stepwise by at least one cycle d1 of the first grating 2. Here, n is a positive integer, and, in the present embodiment, n=4.

The grating movement mechanism 8 includes, for example, a stepping motor or a piezoelectric actuator.

(Generated Image)

Next, with reference to FIG. 2, a description will be made of an image generated by the X-ray phase difference imaging system 100 according to the first embodiment of the present invention.

Figure 2:
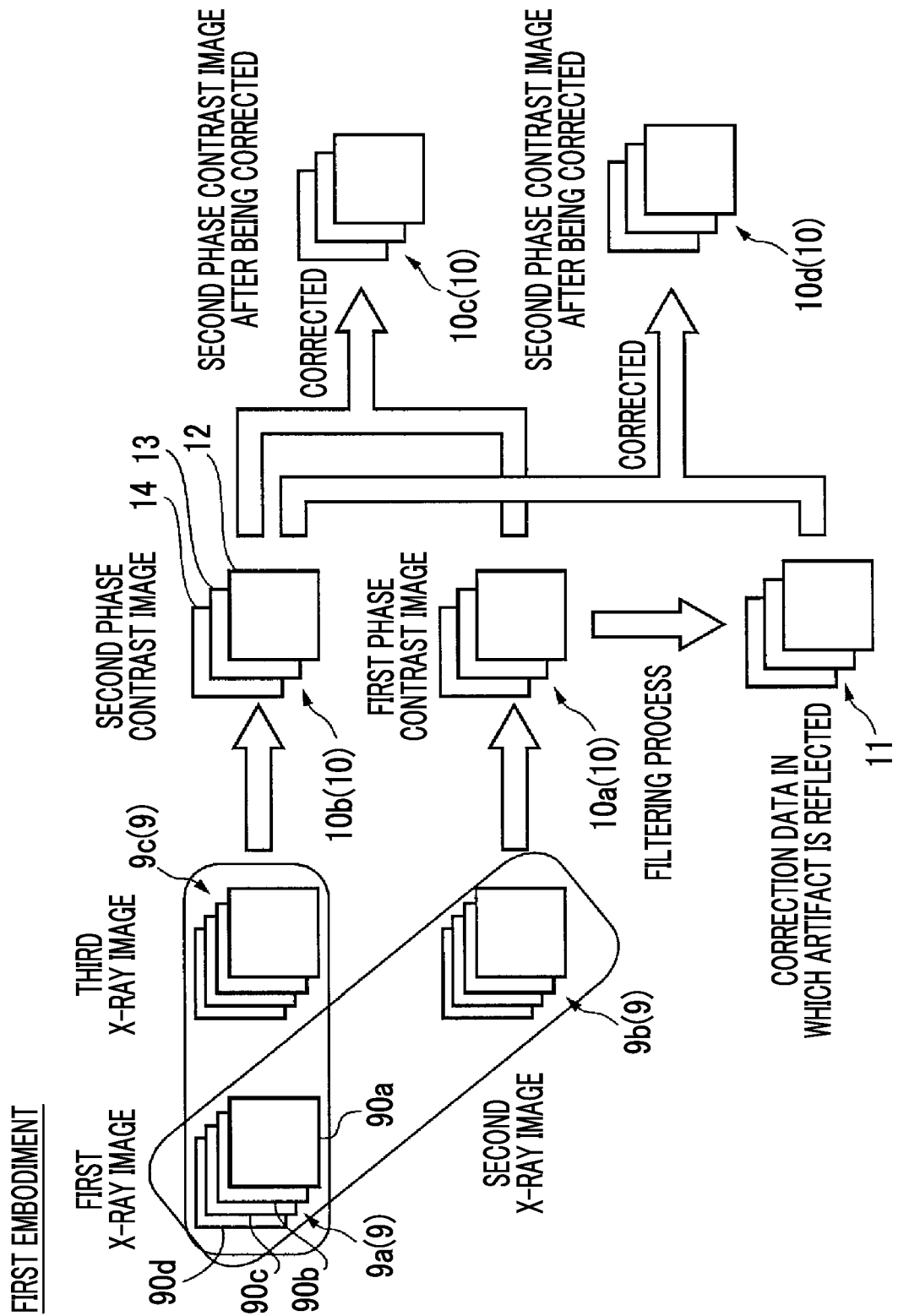
FIG. 2 is a schematic diagram for describing an image captured and an image generated by the X-ray phase difference imaging system according to the first embodiment of the present invention.

FIG. 2 is a schematic diagram illustrating a relationship between images generated and reconstructed by the X-ray phase difference imaging system 100 according to the first embodiment of the present invention.

As illustrated in FIG. 2, in the X-ray phase difference imaging system 100 according to the first embodiment, the first X-ray image 9a, the second X-ray image 9b, and the third X-ray image 9c are captured. The first X-ray image 9a is an image captured in a state in which a subject T is not disposed. The second X-ray image 9b is an image captured in a state in which the subject T is not disposed after the first X-ray image 9a is captured. The third X-ray image 9c is an image captured in a state in which the subject T is disposed after the first X-ray image 9a is captured. In the present embodiment, the X-ray phase difference imaging system 100 is configured to reconstruct the first phase contrast image 10a by using the first X-ray image 9a and the second X-ray image 9b. The X-ray phase difference imaging system 100 is configured to reconstruct the second phase contrast image 10b by using the first X-ray image 9a and the third X-ray image 9c. In the present embodiment, the image processor is configured to generate a dark field image 12, an absorption image 13, and a phase differentiation image 14 according to a 4-step fringe scanning method, and thus FIG. 2 illustrates four X-ray images 9 and three phase contrast images 10.

Here, the phase contrast image 10 is an image generated on the basis of a change in an X-ray due to disposition of the subject T in the X-ray image 9 (the first X-ray image 9a) captured in a state in which the subject T is not disposed and the X-ray image 9 (the third X-ray image 9c) captured in a state in which the subject T is disposed. For example, the dark field image 12 is an image of an internal structure of the subject T generated on the basis of scattering of an X-ray at a minute angle occurring when the X-ray is transmitted through the subject T. The absorption image 13 is an image generated on the basis of a change in the intensity of an X-ray, detected by the detector 4, due to the X-ray being absorbed by the subject T when the X-ray is transmitted through the subject T. For example, the phase differentiation image 14 is an image of the internal structure of the subject T generated on the basis of deviation in a phase of an X-ray occurring when the X-ray is transmitted through the subject T. The term "reconstruction" indicates that the phase contrast image is generated on the basis of a change in an X-ray between the first X-ray image 9a and the third X-ray image 9c.

In the present embodiment, the X-ray phase difference imaging system 100 is configured to correct an artifact of the second phase contrast image 10b on the basis of the first phase contrast image 10a. Specifically, the X-ray phase difference imaging system 100 is configured to acquire correction data 11 in which an artifact is reflected from the first phase contrast image 10a, and to acquire a second phase contrast image 10c obtained by correcting the second phase contrast image 10b by using the acquired correction data 11 in which the artifact is reflected.

Generally, in order to the phase contrast image 10 by using a Talbot interferometer such as the X-ray phase difference imaging system 100, as illustrated in FIG. 2, the first X-ray image 9a captured in a state in which the subject T is not disposed and the third X-ray image 9c captured in a state in which the subject T is disposed are necessary. In a case where the image quality of the first X-ray image 9a is low, an artifact occurs in the generated phase contrast image 10 due to the image quality, and thus it is preferable to generate the phase contrast image 10 by using the high quality first X-ray image 9a. In order to acquire the high quality first X-ray image 9a, it is necessary to increase an exposure time t3 (refer to FIG. 3) when the first X-ray image 9a is captured. However, in a case where the high quality first X-ray image 9a is captured every time the subject T is imaged, the overall imaging time is increased, and thus usability is reduced. Therefore, in order to reduce an imaging time, the first X-ray image 9a captured in a state in which the subject T is not disposed may be acquired in advance during startup of the X-ray phase difference imaging system 100. However, in a case where the first X-ray image 9a is acquired in advance, since a relative position between the first grating 2 and the second grating 3 is deviated due to thermal expansion of a grating holding portion caused by heat generated from the X-ray source 1 or vibration of the grating movement mechanism 8, a probability that an imaging condition may change increases with the passage of time from startup of the X-ray phase difference imaging system 100, and thus a gradational artifact occurs in the generated phase contrast image 10. In order to prevent the gradational artifact from occurring in the phase contrast image 10, it is necessary to perform imaging without disposing the subject T immediately before the subject T is imaged.

Therefore, in the present embodiment, the image processor 6 is configured to capture the second X-ray image 9b in a short period of time before or after the third X-ray image 9c is captured, acquire the correction data 11 in which an artifact caused by a change in an imaging condition is reflected by using the first X-ray image 9a and the second X-ray image 9b acquired during startup of the X-ray phase difference imaging system 100, and correct the second phase contrast image 10b by using the acquired correction data 11. Here, since the first X-ray image 9a and the second X-ray image 9b are images captured in a state in which the subject T is not disposed, nothing may be captured in the first phase contrast image 10a reconstructed from the images in a case where there is no change in an X-ray. However, actually, an imaging condition changes due to a temperature change or the like between capturing of the first X-ray image 9a and capturing of the second X-ray image 9b, and thus an artifact occurs in the first phase contrast image 10a due to the change in the imaging condition. Therefore, the correction data 11 in which the artifact is reflected is acquired from the first phase contrast image 10a such that the second phase contrast image 10b is corrected, and thus it is possible to correct the artifact that occurs in the second phase contrast image 10b due to the change in the imaging condition.

The first X-ray image 9a is an air image for generating the phase contrast image 10, and the second X-ray image 9b is an image captured right after the subject T is imaged. Therefore, the correction data 11 in which an artifact caused by a change in an imaging condition between capturing of the first X-ray image 9a and capturing of the second X-ray image 9b is reflected can be extracted from the first phase contrast image 10a. On the other hand, in a case where the second X-ray image 9b is captured in a short period of time, an exposure time t5 is short, and thus the second X-ray image 9b includes noise. Therefore, the first phase contrast image 10a reconstructed from the first X-ray image 9a and the second X-ray image 9b includes the noise caused by the second X-ray image 9b. In a case where the second phase contrast image 10b is corrected by using the correction data 11 in which an artifact is reflected and which is acquired from the first phase contrast image 10a including the noise, noise increases in the obtained second phase contrast image 10c after being corrected. Therefore, in the present embodiment, the image processor 6 is configured to perform a filtering process on the first phase contrast image 10a so as to remove the noise from the first phase contrast image 10a and thus to reduce noise included in the acquired correction data 11 in which an artifact is reflected. Noise included in a second phase contrast image 10d after being corrected can also be reduced by reducing noise included in the correction data 11 in which an artifact is reflected. A process of acquiring the correction data 11 in which an artifact is reflected from the first phase contrast image 10a and a process of removing noise will be described later.

(Exposure Time and Imaging Time Interval when Each Image is Captured)

Next, with reference to FIG. 3, a description will be made of an exposure time and an imaging time interval when each image is captured.

Figure 3:
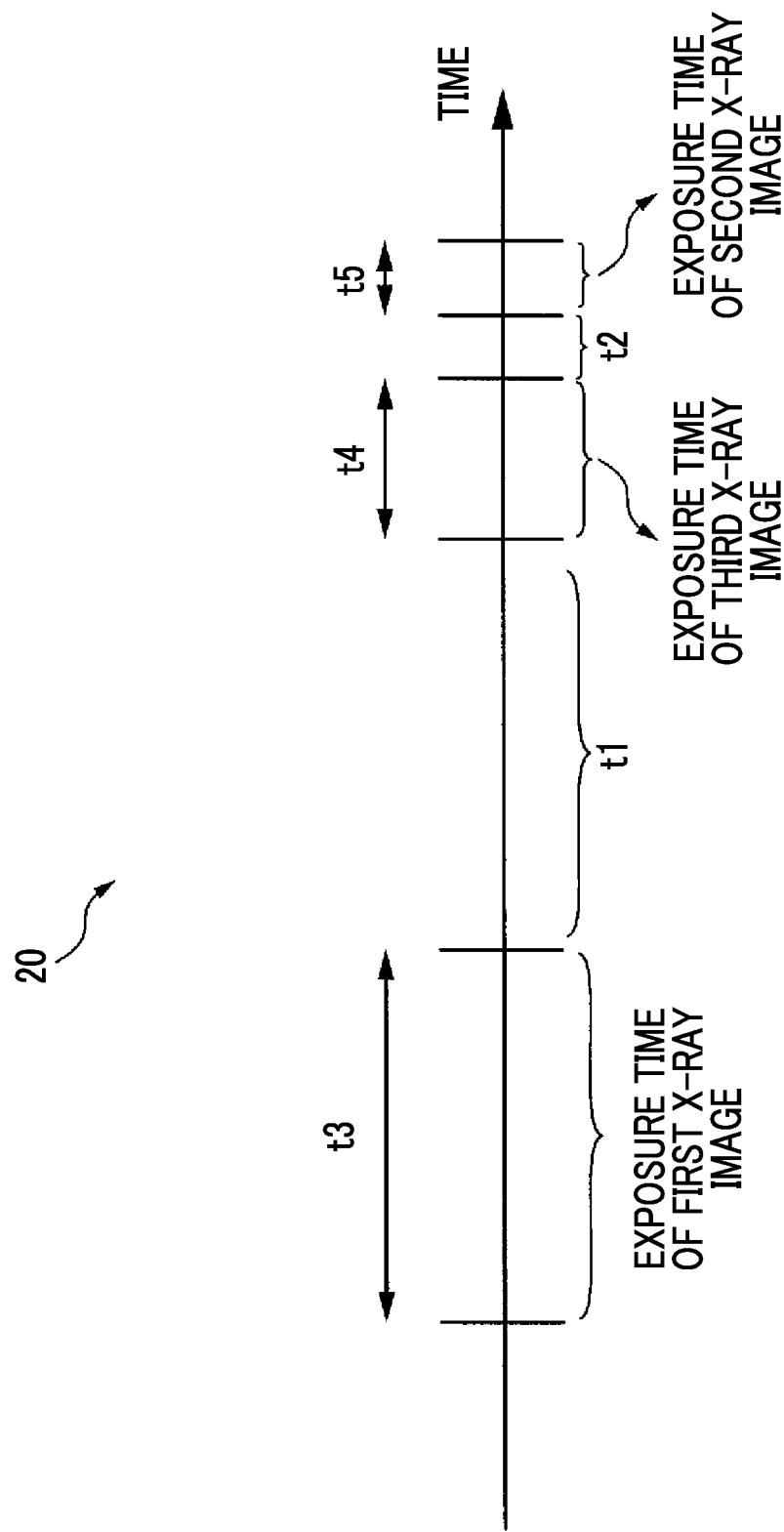
FIG. 3 is a schematic diagram for describing an imaging time interval of an X-ray image captured by the X-ray phase difference imaging system according to the first embodiment of the present invention, and an exposure time when each image is captured.

A number line 20 illustrated in FIG. 3 is a number line in which a transverse axis is a time axis, and expresses an exposure time and an imaging time interval when each image is captured. In the present embodiment, a time t1 illustrated in FIG. 3 is a time indicating a time interval between capturing of the first X-ray image 9a and capturing of the third X-ray image 9c. A time t2 illustrated in FIG. 3 is a time indicating a time interval between capturing of the second X-ray image 9b and capturing of the third X-ray image 9c. Times t3 to t5 illustrated in FIG. 3 respectively indicate exposure times of an X-ray when the first X-ray image 9a, the second X-ray image 9b, and the third X-ray image 9c are captured. The exposure time t3 and the exposure time t5 are respectively examples of a "second exposure time" and a "first exposure time" in the claims.

As illustrated in FIG. 3, in the present embodiment, the first X-ray image 9a, the second X-ray image 9b, and the third X-ray image 9c are captured such that the time interval t2 between capturing of the second X-ray image 9b and the third X-ray image 9c is shorter than the time interval t1 between capturing of the first X-ray image 9a and the third X-ray image 9c. In the present embodiment, capturing of the third X-ray image 9c is performed subsequently to capturing of the second X-ray image 9b. Specifically, capturing of the third X-ray image 9c is performed right after capturing of the second X-ray image 9b. The phrase "right after capturing of the third X-ray image 9c" indicates that imaging is performed within a predetermined time interval after the third X-ray image 9c is captured. The predetermined time interval is a time interval that is within a predetermined time for which an imaging condition may be regarded as substantially not changing with the passage of time (a substantially identical imaging condition may be regarded as being maintained) and which is shorter than a half of the time interval t1 between capturing of the first X-ray image 9a and capturing of the third X-ray image 9c, for the purpose of capturing of the phase contrast image 10. For example, the predetermined time interval is preferably 30 minutes.

Here, as described above, it is necessary to acquire the high quality first X-ray image 9a in order to improve the image quality of the second phase contrast image 10b. Therefore, the exposure time t3 when the first X-ray image 9a is captured is preferably set to a time for which the image quality of the first X-ray image 9a can be improved. The exposure time t3 may be any exposure time as long as the first X-ray image 9a can be obtained to have high image quality. In the example illustrated in FIG. 3, the exposure time t3 is a time longer than t4 and t5, and is a time ten or more times longer than t5. The exposure time t3 may be set to, for example, 8 minutes. On the other hand, the second X-ray image 9b may have image quality allowing a tendency of an artifact occurring in the first phase contrast image 10a to be identified. Therefore, as illustrated in FIG. 3, the exposure time t5 when the second X-ray image 9b is captured is shorter than the exposure time t3 when the first X-ray image 9a is captured. The exposure time t5 may be any exposure time as long as the exposure time is a predetermined time for which the second X-ray image 9b having image quality allowing a tendency of an artifact to be identified can be captured. The exposure time t5 of the second X-ray image 9b may be, for example, 16 seconds. The exposure time t4 of the third X-ray image 9c may be set according to a method of imaging the subject T. In the example illustrated in FIG. 3, the exposure time t4 is set to a time longer than the exposure time t5 of the second X-ray image 9b and shorter than the exposure time t3 of the first X-ray image 9a. The exposure time t4 of the third X-ray image 9c may be set to, for example, one minute.

(Acquired Image and Generated Image)

Next, with reference to FIGS. 4 and 5, a description will be made of an image acquired and an image generated by the X-ray phase difference imaging system 100 according to the present embodiment.

In the present embodiment, the image processor 6 is configured to reconstruct the phase contrast image 10 according to a fringe scanning method. FIG. 4(A) is a schematic diagram illustrating the first X-ray image 9a acquired by the image processor 6. A first X-ray image 90a, a first X-ray image 90b, a first X-ray image 90c, and a first X-ray image 90d illustrated in FIG. 4(A) are images captured while subjecting the second grating 3 to translational movement by d2/4. Since imaging is performed while subjecting the second grating 3 to translational movement, a relative position between the first grating 2 and the second grating 3 differs, and thus moire fringes displayed on the respective images of the first X-ray image 9a are different from each other.

FIG. 4(B) is a schematic diagram illustrating the second X-ray image 9b acquired by the image processor 6. A second X-ray image 91a to a second X-ray image 91d illustrated in FIG. 4(B) are images captured while subjecting the second grating 3 to translational movement by d2/4 in the same manner as the first X-ray image 9a. Moire fringes displayed on the respective images of the second X-ray image 9b are different from each other in the same manner as in the first X-ray image 9a. FIG. 4(B) illustrates an example of a case where positional deviation occurs in a relative position between the first grating 2 and the second grating 3 due to heat generated from the X-ray source 1 or vibration of the grating movement mechanism 8 during the elapse of the time interval t1 in the second X-ray image 9b after the first X-ray image 9a is captured. Thus, moire fringes in each step of the first X-ray image 9a and the second X-ray image 9b are different from each other. The second X-ray image 9b is captured in a short period of time, and thus the exposure time t5 is short, and noise occurs therein.

FIG. 4(C) is a schematic diagram illustrating the first phase contrast image 10a reconstructed by using the first X-ray image 9a and the second X-ray image 9b. Specifically, FIG. 4(C) illustrates the dark field image reconstructed from the first X-ray image 9a and the second X-ray image 9b. As illustrated in FIG. 4(C), an imaging condition changes between capturing of the first X-ray image 9a and capturing of the second X-ray image 9b, and thus a gradational artifact occurs in the dark field image 12. Noise caused by the noise included in the second X-ray image 9b is included in the dark field image 12. For convenience, in FIG. 4(C), noise included during reconstruction is illustrated to be diagonally hatched. In the present embodiment, the image processor 6 is configured to acquire the correction data 11 in which an artifact of the dark field image 12 (first phase contrast image 10a) is reflected, through a filtering process using a low-pass filter. Specifically, the image processor 6 is configured to perform fast Fourier transform (FFT) on the dark field image 12, apply the low-pass filter, and then perform inverse FFT so as to acquire the correction data 11. For example, the image processor 6 acquires a dark field image 12b as illustrated in FIG. 4(D) as the correction data 11 from which noise is removed and in which the gradational artifact is reflected.

In the present embodiment, as illustrated in FIG. 4(D), the image processor 6 is configured to correct the second phase contrast image 10b by using the correction data 11 in which the gradational artifact is reflected by using the first X-ray image 9a and the second X-ray image 9b captured in a state in which the subject T is not disposed. Therefore, even in a case where the subject T is captured in the whole of the second phase contrast image 10b or most of the second phase contrast image 10b, the correction data 11 can be acquired by using the first phase contrast image 10a in which the subject T is not captured. In other words, the correction data 11 can be acquired regardless of a proportion of the subject T occupying the second phase contrast image 10b.

FIG. 5 is a schematic diagram illustrating the second phase contrast image 10b before being corrected and the second phase contrast image 10c after being corrected. Specifically, FIG. 5(A) illustrates a dark field image 12c before being corrected and a dark field image 12d after being corrected. FIG. 5(B) illustrates an absorption image 13a before being corrected and an absorption image 13b after being corrected. FIG. 5(C) illustrates a phase differentiation image 14a before being corrected and a phase differentiation image 14b after being corrected. The subject T is captured in each second phase contrast image 10b in FIG. 5. A dashed line part of the subject T in the phase differentiation image 14a in FIG. 5(C) illustrates, for convenience, a region that is greatly influenced by an artifact and cannot be recognized on the phase contrast image 10.

In the present embodiment, regarding the absorption image 13 and the phase differentiation image 14, in the same manner as in the method of acquiring the correction data 11 in which an artifact of the dark field image 12 is reflected, the image processor 6 is configured to apply a low-pass filter to the first phase contrast image 10a so as to acquire the correction data 11 in which an artifact of the absorption image 13 is reflected and the correction data 11 in which an artifact of the phase differentiation image 14 is reflected, correct the absorption image 13a and the phase differentiation image 14a by using the acquired correction data 11, and acquire the absorption image 13b and the phase differentiation image 14b. In the examples illustrated in FIG. 5, for convenience, a proportion of the subject T occupying the second phase contrast image 10b is illustrated to be small. However, even in a case where the subject T is captured in the whole or most of the second phase contrast image 10b, the correction data 11 in which an artifact is reflected can be acquired on the basis of the first phase contrast image 10a captured in a state in which the subject T is not disposed. Therefore, an artifact of the second phase contrast image 10b can be corrected even in a case where the subject T is captured in the whole or most of the second phase contrast image 10b.

The image processor 6 is configured to perform a correction process on the dark field image 12, the absorption image 13, and the phase differentiation image 14 according to the following Equations (1) to (3).

$$A = Ca * As/LPF(Aa) \quad (1)$$

$$S = Cs * Ss/LPF(Sa) \quad (2)$$

$$P = Cp + Ps - LPF(Pa) \quad (3)$$

Here, S, A, and P respectively indicate the dark field image 12d, the absorption image 13b, and the phase differentiation image 14b after artifacts are corrected. In addition, Ss, As, and Ps respectively indicate the dark field image 12c, the absorption image 13a, and the phase differentiation image 14a before being corrected. Further, Sa, Aa, and Pa respectively indicate the dark field image 12, the absorption image 13, and the phase differentiation image 14 that are reconstructed from the first X-ray image 9a and the second X-ray image 9b and in which the subject T is not captured. Still further, LPF indicates a process of applying a low-pass filter. Moreover, Cs, Ca, and Cp are respectively values set as pixel values of image backgrounds, and, for example, 5000 or 50000 is used.

In the first embodiment, as shown in the above Equations (1) and (2), the image processor 6 is configured to multiply, by a constant, a result obtained by dividing the second phase contrast image 10b in which the subject T is reflected by the first phase contrast image 10a from which noise is removed and in which the subject T is not captured, and thus to correct the dark field image 12 and the absorption image 13. As shown in the above Equation (3), the image processor 6 is configured to add a constant to a result obtained by subtracting the first phase contrast image 10a from which noise is removed from the second phase contrast image 10b and thus to correct the phase differentiation image 14.

(Phase Contrast Image Correction Method)

Figure 6:
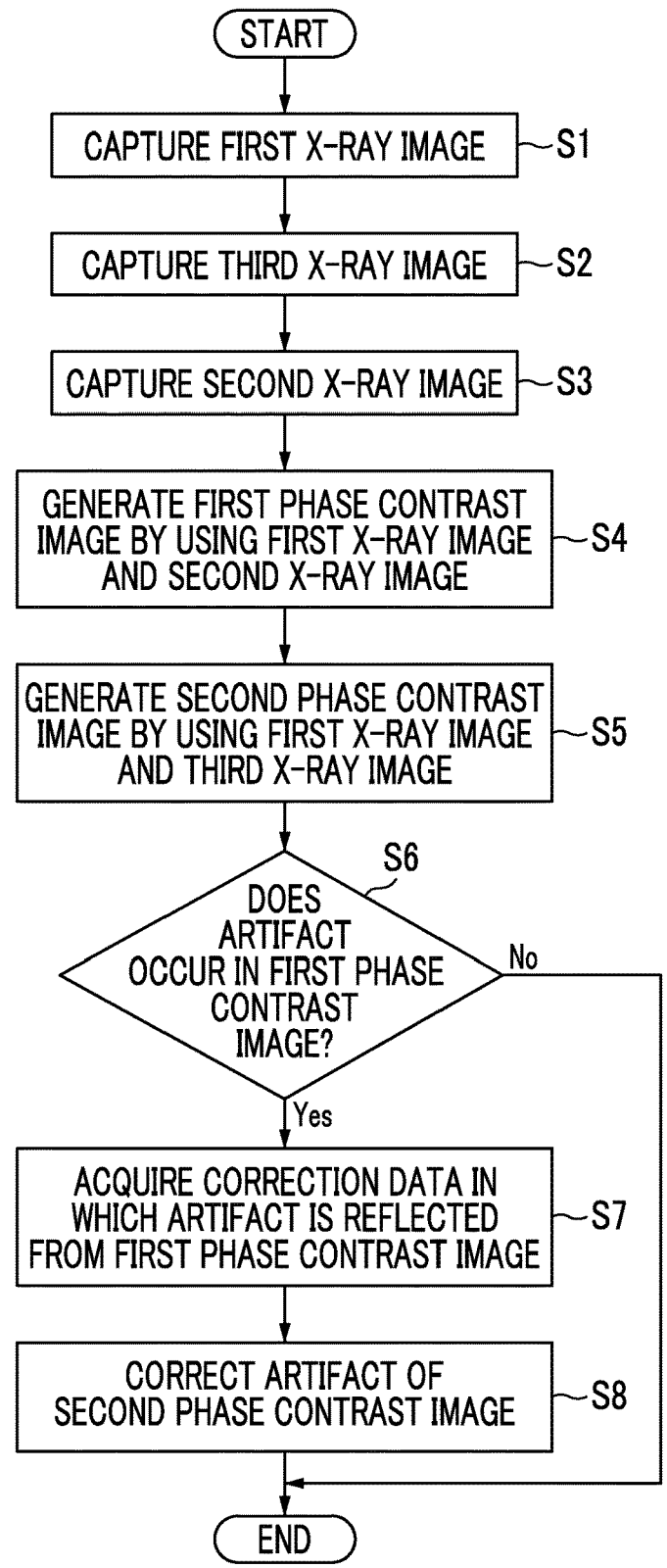
FIG. 6 is a flowchart for describing a phase contrast image correction method according to the first embodiment of the present invention.

Next, with reference to FIG. 6, a description will be made of a method of correcting the phase contrast image 10 according to the present embodiment.

In step S1, the controller 5 captures the first X-ray image 9a in a state in which the subject T is not disposed. Next, in step S2, the controller 5 captures the third X-ray image 9c in a state in which the subject T is disposed. Thereafter, the process proceeds to step S3.

In step S3, the controller 5 captures the second X-ray image 9b in a state in which the subject T is not disposed. Next, in step S4, the image processor 6 reconstructs the first phase contrast image 10a from the first X-ray image 9a and the second X-ray image 9b that are captured such that the time interval t2 between capturing of the second X-ray image 9b and capturing of the third X-ray image 9c is shorter than the time interval t1 between capturing of the first X-ray image 9a and capturing of the third X-ray image 9c. Thereafter, the process proceeds to step S5.

In step S5, the image processor 6 reconstructs the second phase contrast image 10b by using the first X-ray image 9a and the third X-ray image 9c. Next, in step S6, the image processor 6 determines whether or not an artifact occurs in the first phase contrast image 10a. In a case where the artifact occurs in the first phase contrast image 10a, the process proceeds to step S7. In a case where the artifact does not occur in the first phase contrast image 10a, the process is finished.

In step S7, the image processor 6 acquires the correction data 11 in which the artifact is reflected from the first phase contrast image 10a. Next, in step S8, the image processor 6 corrects the artifact of the second phase contrast image 10b by using the acquired correction data 11 in which the artifact is reflected, and finishes the process.

Effects of First Embodiment

In the first embodiment, the following effects can be achieved.

In the first embodiment, as described above, the X-ray phase difference imaging system 100 includes the X-ray source 1; a plurality of gratings that includes the first grating 2 irradiated with an X-ray from the X-ray source 1 and the second grating 3 irradiated with the X-ray from the first grating 2; the detector 4 that detects the X-ray irradiated from the X-ray source 1; and the image processor 6 that generates the phase contrast image 10 by using the X-ray image 9 detected by the detector 4, in which the image processor 6 is configured to acquire the first X-ray image 9a captured in a state in which the subject T is not disposed, acquire the second X-ray image 9b captured in a state in which the subject T is not disposed and the third X-ray image 9c captured in a state in which the subject T is disposed after the first X-ray image 9a is acquired, reconstruct the first phase contrast image 10a by using the first X-ray image 9a and the second X-ray image 9b that are captured such that the time interval t2 between capturing of the second X-ray image 9b and capturing of the third X-ray image 9c is shorter than the time interval t1 between capturing of the first X-ray image 9a and the third X-ray image 9c, reconstruct the second phase contrast image 10b by using the first X-ray image 9a and the third X-ray image 9c, and correct an artifact of the second phase contrast image 10b on the basis of the first phase contrast image 10a.

With this configuration, it is possible to suppress a change in an imaging condition in capturing of the second X-ray image 9b and capturing of the third X-ray image 9c. As a result, it is possible to handle an artifact occurring in the first phase contrast image 10a and an artifact occurring in the second phase contrast image 10b as the substantially same artifact. Therefore, it is possible to correct an artifact caused by a change in an imaging condition on the basis of the first phase contrast image 10a reconstructed by using the first X-ray image 9a and the second X-ray image 9b. Since the first X-ray image 9a and the second X-ray image 9b are images captured in a state in which the subject T is not disposed, even in a case where the subject T is imaged to be captured in the whole or most of a captured image, it is possible to correct an artifact caused by a change in an imaging condition in the second phase contrast image 10b.

In the first embodiment, as described above, of capturing of the second X-ray image 9b and capturing of the third X-ray image 9c, the image processor 6 is configured to perform capturing of the third X-ray image 9c subsequently to capturing of the second X-ray image 9b, and reconstruct the first phase contrast image 10a by using the second X-ray image 9b and the first X-ray image 9a. Consequently, the second X-ray image 9b and the third X-ray image 9c can be successively captured, and thus it is possible to reduce the time interval t2 between capturing of the second X-ray image 9b and capturing of the third X-ray image 9c. As a result, even in a case where an imaging condition changes between capturing of the second X-ray image 9b and capturing of the third X-ray image 9c, it is possible to reduce the influence of an artifact caused by the change in the imaging condition and thus to further improve the correction effect for the second phase contrast image 10b.

In the first embodiment, as described above, the image processor 6 is configured to reconstruct the first phase contrast image 10a by using the second X-ray image 9b captured right after the third X-ray image 9c is captured, and the first X-ray image 9a. Consequently, it is possible to further reduce the time interval t2 between capturing of the second X-ray image 9b and capturing of the third X-ray image 9c. As a result, even in a case where an imaging condition changes between capturing of the second X-ray image 9b and capturing of the third X-ray image 9c, it is possible to further suppress the influence of an artifact caused by the change in the imaging condition and thus to still further improve the correction effect for the second phase contrast image 10b.

In the first embodiment, as described above, the image processor 6 is configured to correct an artifact of the second phase contrast image 10b on the basis of the first phase contrast image 10a that is reconstructed by using the first X-ray image 9a and the second X-ray image 9b that are captured such that the exposure time t5 of the X-ray when the second X-ray image 9b is captured is shorter than the exposure time t3 of the X-ray when the first X-ray image 9a is captured. Consequently, the exposure time t5 is shorter than the exposure time t3, and thus it is possible to reduce an imaging time more than in a case where the third X-ray image 9c is captured after the first X-ray image 9a is captured.

In the first embodiment, as described above, the exposure time t5 is a predetermined time for which the second X-ray image 9b having image quality allowing a tendency of an artifact to be identified can be captured. Here, the first X-ray image 9a preferably has high image quality in order to improve the image quality of the second phase contrast image 10b. On the other hand, the second X-ray image 9b may have the lowest image quality since a tendency of an artifact has only to be identifiable in the first phase contrast image 10a. Therefore, the exposure time t5 can be made shorter in a range in which a tendency of an artifact is identifiable, and thus an imaging time can be further reduced.

In the first embodiment, as described above, an artifact of the phase contrast image 10 is a gradational artifact occurring in the first phase contrast image 10a and the second phase contrast image 10b. Consequently, since an artifact caused by a change in an imaging condition with the passage of time is gradational, the present embodiment is irradiated, and thus it is possible to effectively correct the gradational artifact occurring in the second phase contrast image 10b.

In the first embodiment, as described above, the image processor 6 is configured to acquire the correction data 11 in which an artifact of the first phase contrast image 10a is reflected through a filtering process using a low-pass filter. Consequently, noise of the first phase contrast image 10a can be removed through the filtering process, and thus an artifact can be corrected without increasing noise of the second phase contrast image 10b.

In the first embodiment, as described above, the phase contrast image correction method includes a step of capturing the first X-ray image 9a in a state in which the subject T is not disposed; a step of capturing the second X-ray image 9b in a state in which the subject T is not disposed; a step of capturing the third X-ray image 9c in a state in which the subject T is disposed after the second X-ray image 9b is captured; a step of reconstructing the first phase contrast image 10a by using the first X-ray image 9a and the second X-ray image 9b that are captured such that the time interval t2 between capturing of the second X-ray image 9b and capturing of the third X-ray image 9c is shorter than the time interval t1 between capturing of the first X-ray image 9a and the third X-ray image 9c; a step of reconstructing the second phase contrast image 10b by using the first X-ray image 9a and the third X-ray image 9c; and a step of correcting an artifact of the second phase contrast image 10b on the basis of the first phase contrast image 10a. Consequently, the second X-ray image 9b and the third X-ray image 9c can be captured in a state in which an imaging condition does not change. As a result, it is possible to provide the phase contrast image correction method capable of correcting an artifact caused by a change in an imaging condition on the basis of the first phase contrast image 10a reconstructed by using the first X-ray image 9a and the second X-ray image 9b. Since the first X-ray image 9a and the second X-ray image 9b are images captured in a state in which the subject T is not disposed, even in a case where the subject T is imaged to be captured in the whole or most of a captured image, it is possible to provide the phase contrast image correction method capable of correcting an artifact caused by a change in an imaging condition in the second phase contrast image 10b.

Second Embodiment

Figure 7:
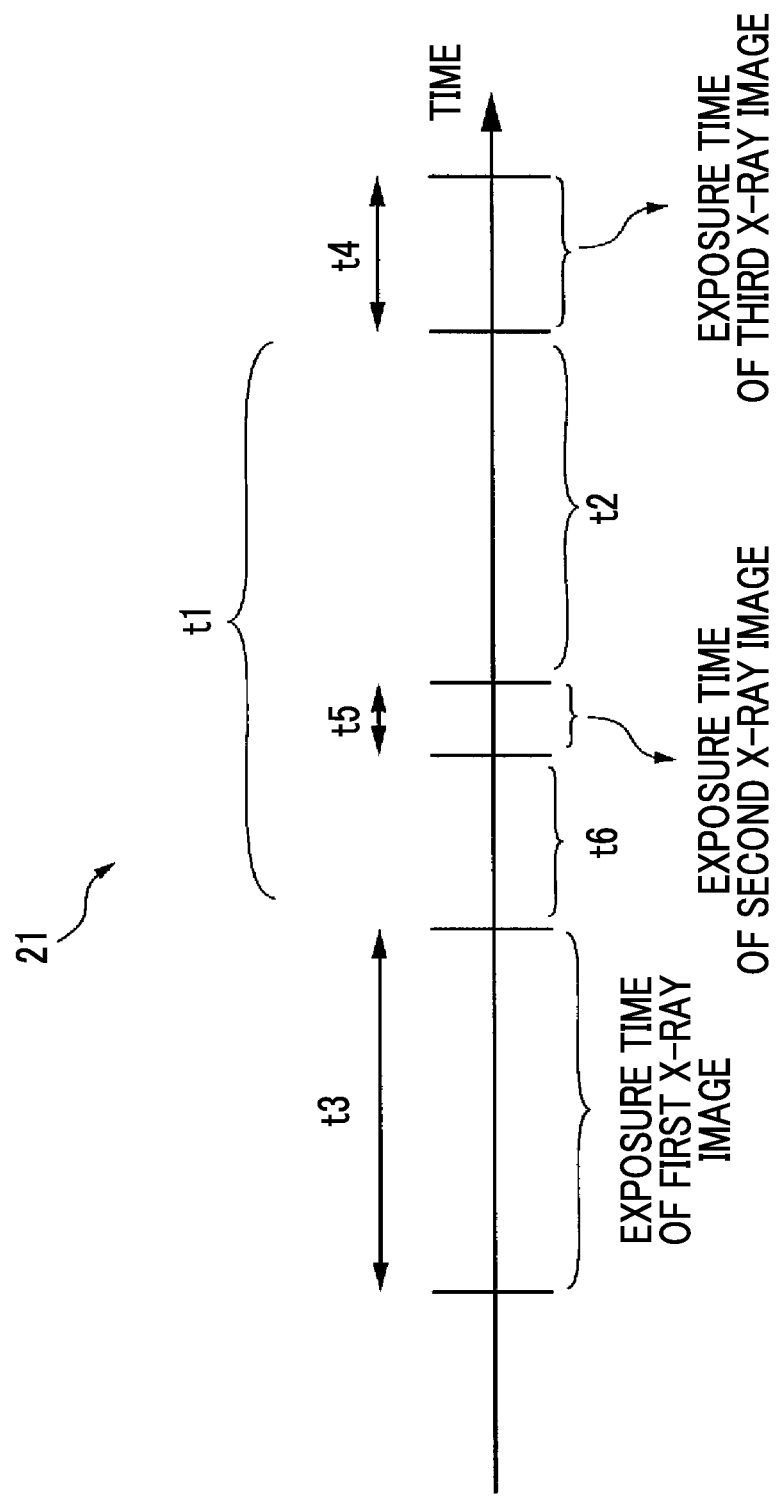
FIG. 7 is a schematic diagram for describing an imaging time interval of an X-ray image captured by the X-ray phase difference imaging system according to a second embodiment of the present invention, and an exposure time when each image is captured.

Next, with reference to FIGS. 1 and 7, a description will be made of an X-ray phase difference imaging system 200 according to a second embodiment of the present invention. Unlike the first embodiment of reconstructing the first phase contrast image 10a by using the first X-ray image 9a and the second X-ray image 9b that are captured such that the time interval t2 between capturing of the second X-ray image 9b and capturing of the third X-ray image 9c is shorter than the time interval t1 between capturing of the first X-ray image 9a and the third X-ray image 9c, in the second embodiment, the X-ray phase difference imaging system 200 is configured to reconstruct the first phase contrast image 10a by using the first X-ray image 9a and the second X-ray image 9b regardless of lengths of the time interval t2 between capturing of the second X-ray image 9b and capturing of the third X-ray image 9c and the time interval t1 between capturing of the first X-ray image 9a and the third X-ray image 9c. The same constituent element as that in the first embodiment will be given the same reference numeral, and a description thereof will not be repeated.

In the second embodiment, the image processor 6 is configured to acquire the first X-ray image 9a captured in a state in which the subject T is not disposed, acquire the second X-ray image 9b captured in a state in which the subject T is not disposed and the third X-ray image 9c captured in a state in which the subject T is disposed after the first X-ray image 9a is acquired, reconstruct the first phase contrast image 10a by using the first X-ray image 9a and the second X-ray image 9b, reconstruct the second phase contrast image 10b by using the first X-ray image 9a and the third X-ray image 9c, and correct an artifact of the second phase contrast image 10b on the basis of the first phase contrast image 10a. In the second embodiment, for example, as in a number line 21 illustrated in FIG. 7, the image processor 6 may acquire the correction data 11 in which an artifact caused by a change in an imaging condition for a time interval t6 between capturing of the first X-ray image 9a and the second X-ray image 9b is reflected from the first phase contrast image 10a even in a case where the time interval t2 between capturing of the second X-ray image 9b and capturing of the third X-ray image 9c is longer than the time interval t6 between capturing of the first X-ray image 9a and the second X-ray image 9b, and may correct the second phase contrast image 10b on the basis of the acquired correction data 11.

Remaining configurations of the second embodiment are the same as those of the first embodiment.

Effects of Second Embodiment

In the second embodiment, the following effects can be achieved.

In the second embodiment, as described above, the X-ray phase difference imaging system includes the X-ray source 1; a plurality of gratings that includes the first grating 2 irradiated with an X-ray from the X-ray source 1 and the second grating 3 irradiated with the X-ray from the first grating 2; the detector 4 that detects the X-ray irradiated from the X-ray source 1; and the image processor 6 that generates the phase contrast image 10 by using the X-ray image 9 detected by the detector 4, in which the image processor 6 is configured to acquire the first X-ray image 9a captured in a state in which the subject T is not disposed, acquire the second X-ray image 9b captured in a state in which the subject T is not disposed and the third X-ray image 9c captured in a state in which the subject T is disposed after the first X-ray image 9a is acquired, reconstruct the first phase contrast image 10a by using the first X-ray image 9a and the second X-ray image 9b, reconstruct the second phase contrast image 10b by using the first X-ray image 9a and the third X-ray image 9c, and correct an artifact of the second phase contrast image 10b on the basis of the first phase contrast image 10a. Consequently, it is possible to correct an artifact caused by a change in an imaging condition on the basis of the first phase contrast image 10a reconstructed by using the first X-ray image 9a and the second X-ray image 9b. Since the first X-ray image 9a and the second X-ray image 9b are images captured in a state in which the subject T is not disposed, even in a case where the subject T is imaged to be captured in the whole or most of a captured image, it is possible to correct an artifact caused by a change in an imaging condition in the second phase contrast image 10b.

Modification Examples

It is considered that the embodiments disclosed here are exemplary and are not limited in any aspect. The scope of the present invention is exhibited not by the description of the embodiments but by the claims, and includes all changes (modification examples) within the claims and the meaning and the scope of equivalents thereof.

Figure 8:
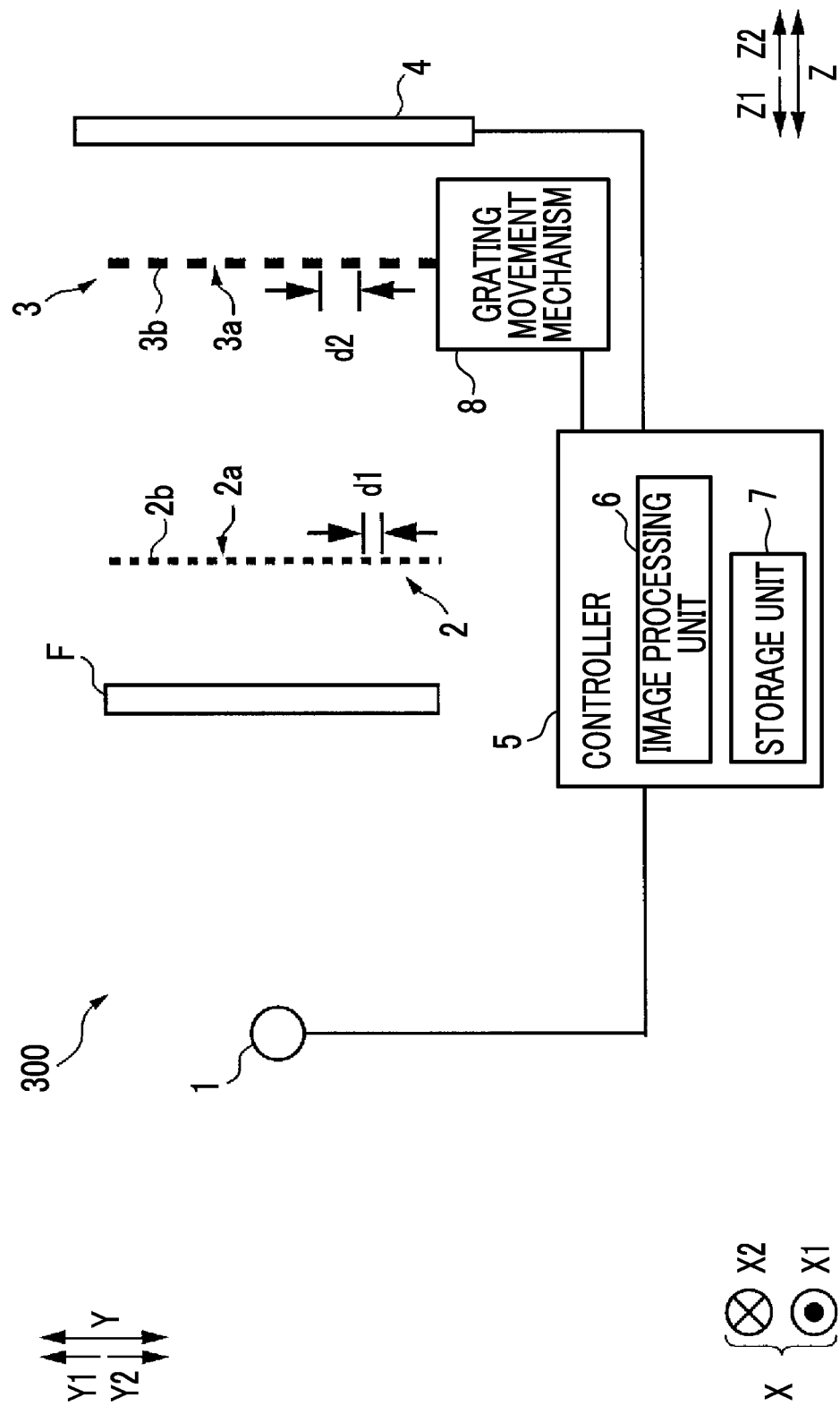
FIG. 8 is a schematic diagram in which an X-ray phase difference imaging system according to a first modification example of the first embodiment of the present invention is viewed from the X direction.

For example, in the first and second embodiments, when the first X-ray image 9a and the second X-ray image 9b are captured, a description has been made of an example in which the images are captured in a state in which the subject T is not disposed, but the present invention is not limited thereto. For example, as in an X-ray phase difference imaging system 300 illustrated in FIG. 8, when the first X-ray image 9a and the second X-ray image 9b are captured, a phantom F having the same extent of X-ray absorption characteristics as those of the subject T may be disposed between the X-ray source 1 and the first grating 2, and the images may be captured. With this configuration, a spectrum of an X-ray detected by the detector 4 when the subject T is disposed and is imaged and a spectrum of an X-ray detected by the detector 4 when the phantom F is disposed and is imaged are equivalent energy spectra, and thus occurring artifacts are also equivalent to each other. Therefore, the phantom F is disposed when the first X-ray image 9a and the second X-ray image 9b are captured, and thus it is possible to improve the effect of correcting an artifact of the second phase contrast image 10b. In a case where the phantom F is disposed and is imaged when the first X-ray image 9a is contact, the phantom F may not be disposed when the second X-ray image 9b is captured. It is possible to improve a correction effect even though the phantom F is not disposed when the second X-ray image 9b is captured.

Figure 9:
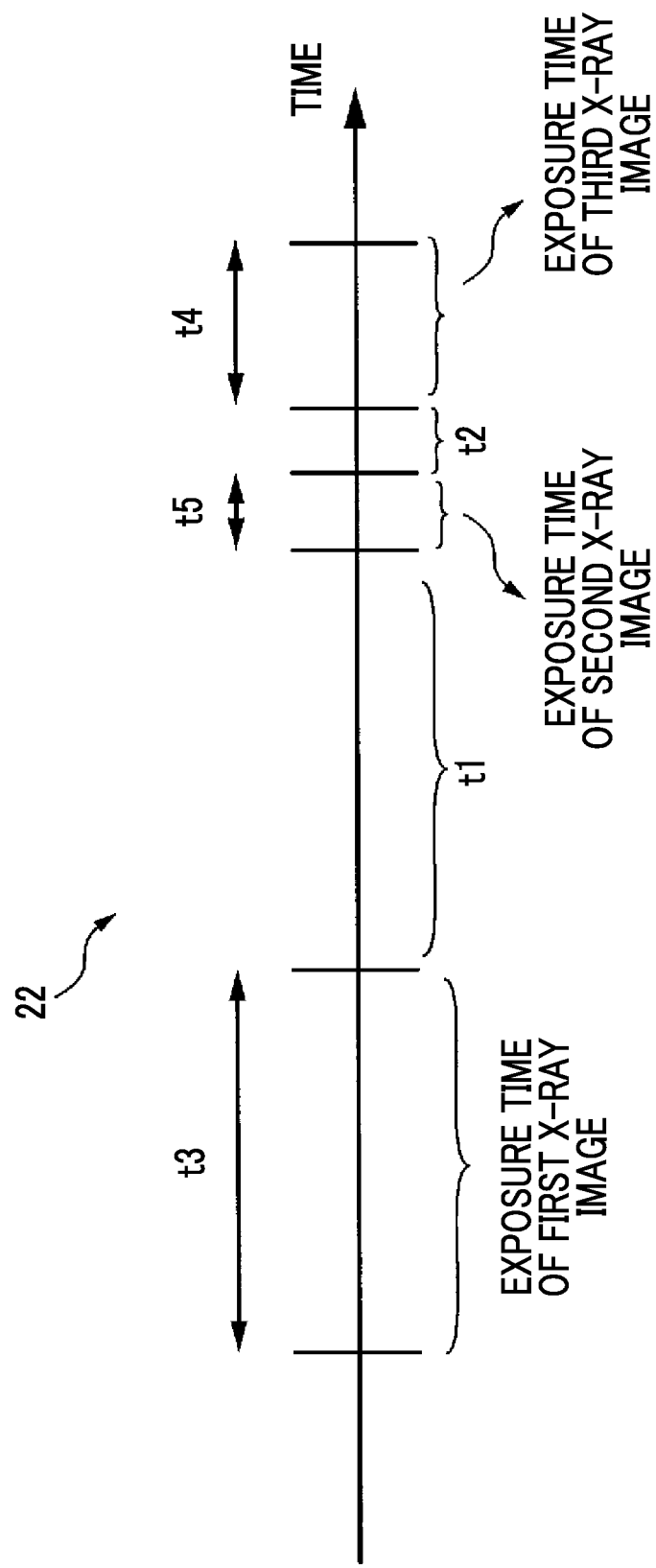
FIG. 9 is a schematic diagram for describing an imaging time interval of an X-ray image captured by an X-ray phase difference imaging system according to a second modification example of the first embodiment of the present invention, and an exposure time when each image is captured.

In the first and second embodiments, a description has been made of an example in which the second X-ray image 9b is captured after the third X-ray image 9c is captured, but the present invention is not limited thereto. For example, as in a number line 22 illustrated in FIG. 9, of capturing of the second X-ray image 9b and capturing of the third X-ray image 9c, capturing of the third X-ray image 9c may be performed after capturing of the second X-ray image 9b. In other words, the second X-ray image 9b may be captured right before the third X-ray image 9c is captured.

In the first and second embodiments, a description has been made of an example in which a filtering process using a low-pass filter is performed when the correction data 11 in which an artifact is reflected is acquired, the present invention is not limited thereto. For example, a filtering process using a smoothing filter may be performed. As the smoothing filter, for example, a Gaussian filter may be used.

There may be a configuration in which, when the correction data 11 in which an artifact is reflected is acquired, the image processor 6 acquires the correction data 11 in which an artifact of the first phase contrast image 10a is reflected by using a polynomial expression including at least a linear function or a quadratic function. In a case where the correction data 11 in which an artifact of the first phase contrast image 10a is reflected is acquired by using a polynomial expression, the image processor 6 may be configured to acquire the correction data 11 in which an artifact of the first phase contrast image 10a is reflected on the basis of pixel values of a plurality of regions in the first phase contrast image 10a.

For example, in a case where the correction data 11 is acquired by using $ax+by+c$ as a linear function, image values of at least three regions are required to obtain the coefficients a, b, and c. Therefore, as illustrated in FIG. 10(A), pixel values of at least a region 30a to a region 30c may be acquired from the first phase contrast image 10a, and the correction data 11 may be acquired on the basis of the linear expression. In a case where the correction data 11 is acquired by using $ax^2+by^2+cxy+dx+ey+f$ as a quadratic function, image values of at least six regions are required to obtain the coefficients a to f. Therefore, as illustrated in FIG. 10(B), pixel values of at least regions 31a to 31f may be acquired from the first phase contrast image 10a, and the correction data 11 may be acquired on the basis of the quadratic expression. The regions 30a to 30c and 31a to 31f from which pixel values are acquired are not limited to the examples illustrated in FIGS. 10(A) and 10(B). Pixel values acquired from any regions may be used as long as the correction data 11 in which an artifact occurring in the first phase contrast image 10a is reflected can be obtained.

In a case where the image processor 6 is configured to acquire the correction data 11 in which an artifact of the first phase contrast image 10a is reflected by using a polynomial expression including at least a linear function or a quadratic function, it is possible to acquire the correction data 11 in which an artifact is easily reflected by using the polynomial expression. In a case where the image processor 6 is configured to acquire the correction data 11 in which an artifact of the first phase contrast image 10a is reflected on the basis of pixel values of a plurality of regions (the region 30a to the region 30c, and the region 31a to the region 31f) in the first phase contrast image 10a, it is possible to acquire the more accurate correction data 11 in which the artifact is reflected.

In the first and second embodiments, a description has been made of an example in which the first grating 2 and the second grating 3 are provided as a plurality of gratings, but the present invention is not limited thereto. For example, as in an X-ray phase difference imaging system 400 illustrated in FIG. 11, a third grating 40 may be provided between the X-ray source 1 and the first grating 2. The third grating 40 has a plurality of slits 40a and X-ray absorption portions 40b arranged in a predetermined cycle (pitch) d3 in the Y direction. Each of the slits 40a and the X-ray absorption portions 40b is formed to linearly extend. Each of the slits 40a and the X-ray absorption portions 40b is formed to extend in parallel. The third grating 40 is disposed between the X-ray source 1 and the first grating 2, and is thus irradiated with an X-ray from the X-ray source 1. The third grating 40 is configured to convert an X-ray having passed through each slit 40a to be used as a linear light source corresponding to a position of each slit 40a. Consequently, the third grating 40 can increase coherence of an X-ray irradiated from the X-ray source 1. Consequently, it is possible to increase coherence of an X-ray irradiated from the X-ray source 1 by using the third grating 40. As a result, a self-image of the first grating 2 can be formed without depending on a focal diameter of the X-ray source 1, and thus it is possible to improve the degree of freedom of selection of the X-ray source 1.

In the first and second embodiments, a description has been made of an example in which the image processor 6 reconstructs the phase contrast image 10 according to the fringe scanning method, but the present invention is not limited thereto. For example, the phase contrast image 10 may be generated according to a moire single shot method in which any one of a plurality of gratings is rotated in the XY plane such that a moire fringe is formed, and imaging is performed. The phase contrast image 10 may be generated according to a Fourier transform method.

The invention claimed is:
1. An X-ray phase difference imaging system comprising:
an X-ray source;
a plurality of gratings that include a first grating irradiated with an X-ray from the X-ray source, and a second grating irradiated with the X-ray from the first grating;
a detector that detects the X-ray irradiated from the X-ray source; and
an image processor that generates a phase contrast image by using an X-ray image detected by the detector,
wherein the image processor is configured to
acquire a first X-ray image captured in a state in which a subject is not disposed,
acquire a second X-ray image captured in a state in which the subject is not disposed and a third X-ray image captured in a state in which the subject is disposed after the first X-ray image is acquired,
reconstruct a first phase contrast image by using the first X-ray image and the second X-ray image that are captured such that a time interval between capturing of the second X-ray image and capturing of the third X-ray image is shorter than a time interval between capturing of the first X-ray image and capturing of the third X-ray image,
reconstruct a second phase contrast image by using the first X-ray image and the third X-ray image, and
correct an artifact of the second phase contrast image on the basis of the first phase contrast image.

2. The X-ray phase difference imaging system according to claim 1,
wherein the image processor is configured to reconstruct the first phase contrast image by using the second X-ray image that is captured in a manner that one of capturing of the second X-ray image and capturing of the third X-ray image is performed and subsequently the other is performed, and the first X-ray image.

3. The X-ray phase difference imaging system according to claim 2,
wherein the image processor is configured to reconstruct the first phase contrast image by using the second X-ray image captured right before or right after the third X-ray image is captured, and the first X-ray image.

4. The X-ray phase difference imaging system according to claim 1,
wherein the image processor is configured to correct an artifact of the second phase contrast image on the basis of the first phase contrast image reconstructed by using the first X-ray image and the second X-ray image that are captured such that a first exposure time of the X-ray when the second X-ray image is captured is shorter than a second exposure time of the X-ray when the first X-ray image is captured.

5. The X-ray phase difference imaging system according to claim 4,
wherein the first exposure time is a predetermined time for which the second X-ray image having image quality allowing a tendency of an artifact to be identified can be captured.

6. The X-ray phase difference imaging system according to claim 1, further comprising:
a storage that stores the first X-ray image,
wherein the image processor is configured to reconstruct the first phase contrast image and the second phase contrast image by using the first X-ray image stored in the storage.

7. The X-ray phase difference imaging system according to claim 1,
wherein an artifact of the phase contrast image is a gradational artifact occurring in the first phase contrast image and the second phase contrast image.

8. The X-ray phase difference imaging system according to claim 1,
wherein the image processor is configured to acquire correction data in which an artifact of the first phase contrast image is reflected, by using a polynomial expression including at least a linear function or a quadratic function.

9. The X-ray phase difference imaging system according to claim 8,
wherein the image processor is configured to acquire the correction data in which the artifact of the first phase contrast image is reflected, on the basis of pixel values of a plurality of regions in the first phase contrast image.

10. The X-ray phase difference imaging system according to claim 1,
wherein the image processor is configured to acquire correction data in which an artifact of the first phase contrast image is reflected, through a filtering process using at least a smoothing filter or a low-pass filter.

11. The X-ray phase difference imaging system according to claim 1,
wherein the plurality of gratings further include a third grating that is disposed between the X-ray source and the first grating.

12. An X-ray phase difference imaging system comprising:
an X-ray source;
a plurality of gratings that include a first grating irradiated with an X-ray from the X-ray source, and a second grating irradiated with the X-ray from the first grating;
a detector that detects the X-ray irradiated from the X-ray source; and
an image processor that generates a phase contrast image by using an X-ray image detected by the detector,
wherein the image processor is configured to
acquire a first X-ray image captured in a state in which a subject is not disposed,
acquire a second X-ray image captured in a state in which the subject is not disposed and a third X-ray image captured in a state in which the subject is disposed after the first X-ray image is acquired,
reconstruct a first phase contrast image by using the first X-ray image and the second X-ray image,
reconstruct a second phase contrast image by using the first X-ray image and the third X-ray image, and
correct an artifact of the second phase contrast image on the basis of the first phase contrast image.

13. A phase contrast image correction method comprising:
capturing a first X-ray image in a state in which a subject is not disposed;
capturing a second X-ray image in a state in which the subject is not disposed;
capturing a third X-ray image in a state in which the subject is disposed before or after the second X-ray image is captured;
reconstructing a first phase contrast image by using the first X-ray image and the second X-ray image that are captured such that a time interval between capturing of the second X-ray image and capturing of the third X-ray image is shorter than a time interval between capturing of the first X-ray image and capturing of the third X-ray image;
reconstructing a second phase contrast image by using the first X-ray image and the third X-ray image; and
correcting an artifact of the second phase contrast image on the basis of the first phase contrast image.

* * * * *